US008383550B2

(12) United States Patent
Bickers et al.

(10) Patent No.: US 8,383,550 B2
(45) Date of Patent: Feb. 26, 2013

(54) DEFOLIANT

(75) Inventors: Udo Bickers, Kelkheim (DE); Frank Sixl, Rechtsupweg (DE)

(73) Assignee: Bayer Cropscience AG, Monheim (DE)

( * ) Notice: Subject to any disclaimer, the term of this patent is extended or adjusted under 35 U.S.C. 154(b) by 252 days.

(21) Appl. No.: 12/751,578

(22) Filed: Mar. 31, 2010

(65) Prior Publication Data

US 2010/0311587 A1 Dec. 9, 2010

(30) Foreign Application Priority Data

Apr. 7, 2009 (EP) .................................... 09005078

(51) Int. Cl.
*A01N 31/02* (2006.01)
*A01N 41/10* (2006.01)
(52) U.S. Cl. ...................................................... 504/162
(58) Field of Classification Search ................... 504/162
See application file for complete search history.

(56) References Cited

U.S. PATENT DOCUMENTS 6,274,535 B1 * 8/2001 Feurer et al. ................... 504/128
6,316,387 B1 * 11/2001 Huff et al. ..................... 504/134

OTHER PUBLICATIONS

International Search Report of PCT/EP2010/001998 mailed Sep. 6, 2010.

* cited by examiner

*Primary Examiner* — Rebecca Prouty
*Assistant Examiner* — Danielle Sullivan
(74) *Attorney, Agent, or Firm* — Baker Donelson Bearman Caldwell & Berkowitz, PC

(57) ABSTRACT

A mixture, comprising
(A) thidiazuron (or thidiazuron and diuron), and
(B) one or more compounds from the group of the herbicidal 1,2,4-triazinone, preferably metribuzin and/or metamitron,
is suitable for use as a defoliant and/or a composition for reducing regrowth, in particular in crops of cotton.

14 Claims, No Drawings

DEFOLIANT

CROSS REFERENCE TO RELATED APPLICATIONS

This application claims priority from European Patent Application No. 09005078.2, filed Apr. 7, 2009, the content of which is incorporated herein by reference in its entirety.

BACKGROUND OF THE INVENTION

1. Field of the Invention

The invention relates to the field of defoliants, in particular thidiazuron-containing mixtures, and their use in crops of cotton.

2. Description of Related Art

Thidiazuron has been known for some time as a defoliant, in particular for use in crops of cotton (see, for example, "The ePesticide Manual". Version 4.0, 2006-07 or "The Pesticide Manual", 14th edition, British Crop Protection Council, Hampshire 2006).

The use of thidiazuron in mixtures has also been described, see, for example, DE 26 46 712 A.

However, since the economical and ecological demands placed on modern defoliants are constantly being raised, for example with respect to effect, application rate, residues, toxicity and favorable manufacturing, there exists the permanent task of developing, for example by combining known active ingredients, novel defoliants which offer, at least in some areas, advantages compared with the known compounds.

SUMMARY OF THE INVENTION

Surprisingly, it has been found that thidiazuron and already commercially used mixtures of thidiazuron and diuron in a mixture with compounds from the group of the herbicidal 1,2,4-triazinone have synergistic effects.

In addition, it has surprisingly been found that compounds from the group of the herbicidal 1,2,4-triazinone in combination with thidiazuron-containing preparations considerably reduce the regrowth of plants, preferably useful plants, particularly preferably cotton.

The present invention accordingly provides a mixture comprising
(A) thidiazuron, and
(B) one or more compounds from the group of the herbicidal 1,2,4-triazinone.

DETAILED DESCRIPTION OF A PREFERRED EMBODIMENT

The abovementioned mixture may also comprise the mixture of thidiazuron and diuron as component (A).

The mixtures according to the invention are suitable in particular for use as defoliants in crops of cotton, due, for example, to rapid action and/or increased activity or lower application rates.

For the purpose of the invention, the term defoliant is synonymous with "defoliant" and "desiccant" and also embraces the known growth-regulating effect of thidiazuron and mixtures comprising thidiazuron.

The active ingredients (a.i.) thidiazuron and diuron used for component (A) are known and commercially available: thidiazuron and diuron from Bayer Crop Science. Mixtures of thidiazuron and diuron are commercially available, for example, under the name ®Droop Ultra (Bayer Crop Science). Such mixtures are described, for example, in U.S. Pat. No. 4,613,354 A.

The active ingredients, with specifications about their preparation, mixing and handling, are described, for example in "The Pesticide Manual", 14th edition (see above), and they are listed under the following entry numbers: Thidiazuron 814, Diuron 291. The preferred component (A) is thidiazuron.

The compounds that can be used for component (B) belong to the chemical class of the herbicidal 1,2,4-triazinones. This group and its activity as herbicides are known and described, for example, in "The Pesticide Manual" (see above). Important active ingredients (a.i.) from this group are metribuzin and metamitron. They are commercially available: metribuzin and metamiton from Bayer Crop Science.

Together with information on preparation, mixing and handling, the active ingredients are described, for example, in "The Pesticide Manual" (see above), where they are listed under the following entry numbers: metribuzin 573 and metamitron 540. Preferred as component (B) are metribuzin and metamitron, particularly preferably metribuzin.

The combination of the active ingredients can be used in a manner which is customary per se, for example by spray application of a spray liquor prepared from individual formulations of the active ingredients in a tank mix or of a spray liquor prepared from a mixed formulation of the active ingredients by dilution with water. Methods which are suitable for the application are in particular those which are customary for the application of the individual active ingredients and which allow a joint application.

In principle, the application can also be carried out by successive applications of the individual active ingredients (components), where the possible interval can be determined in simple routine preliminary trials. However, preference is given to joint application. If appropriate, the active ingredients can also be used in combination with other crop protection agents.

While having the same effect, the application rate of an individual active ingredient in the combination is considerably reduced compared with the application rate of the individual active ingredient in question when used on its own. The optimum choice of the ratio by weight and the application rates depends, for example, on the development stage, on environmental factors and climatic conditions or else on the type of the active crop-protective agents which are additionally employed, if appropriate, and can be determined quickly by the person skilled in the art in simple routine trials.

The application rate for component (A) is generally in the range from 1 to 500 g of active ingredient (=a.i.)/ha.

For thidiazuron, it is preferably in the range from 10 to 500 g of a.i./ha, particularly preferably from 10 to 300 g of a.i./ha, very particularly preferably from 20 to 200 g of a.i./ha, especially preferably from 20 to 150 g of a.i./ha.

In the case of thidiazuron/diuron mixtures (typically in a ratio by weight of 2:1), the application rate is in the general range from 10 to 500 g of a.i./ha, preferably at from 15 to 300 g of a.i./ha, particularly preferably in the range from 20 to 200 g of a.i./ha, particularly preferably from 30 to 200 g of a.i./ha, in particular from 30 to 150 g of a.i./ha.

The application rates for the component (B) can vary within wide limits, depending on the active ingredient, and they are generally between 0.1 and 5000 g of a.i./ha. Preferred application rates for the component (B) are, for example (metribuzin and/or metamitron): from 1 to 1000 g of a.i./ha, particularly preferably from 5 to 500 g of a.i./ha.

The ratios by weight of components (A):(B) can vary within wide limits, in general, they are between 1:100 and 100:1.

The approximate ratio of (A):(B) is preferably 1:0.1-10, particularly preferably 1:0.5-2.

The invention also provides defoliants, i.e. compositions for effecting leaf abscission, which defoliants comprise combinations of active ingredients (A) and (B) and customary formulation auxiliaries (C).

The combinations according to the invention and their individual active ingredients can be formulated in various ways, depending on the prevailing biological and/or chemico-physical parameters. Examples of possible suitable formulations are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, such as dispersion in oil (oil-containing suspension concentrate. OD), solutions which are miscible with oils, capsule suspensions (CS), dusts (DP), granules (GR) in the form of microgranules, spray granules, coated granules and adsorption granules, water-dispersible granules (WG), water-soluble granules (SG), ULV (ultra-low-volume) formulations, microcapsules and WSBs (water-soluble bags).

The individual types of formulation are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ, Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4th Ed. 1986.

Based on these formulations, it is also possible to prepare combinations with other crop protection agents, such as, for example, insecticides, acaricides, herbicides, fungicides, safeners, other growth regulators and/or fertilizers, for example in the form of a ready mix or a tank mix.

In addition, depending on the intended application, it may also be advantageous to add, separately, further formulation auxiliaries (C) and/or further additives, such as, for example, adjuvants, such as, for example, ®Actirob B, from Novance.

Wettable powders are preparations which are uniformly dispersible in water and which, besides the active ingredient, also comprise ionic and/or nonionic surfactants (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalene-sulfonate or else sodium oleoylmethyl-taurinate, in addition to a diluent or inert substance. To prepare the wettable powders, the active ingredients are ground finely, for example in customary equipment such as hammer mills, blower mills and air-jet mills, and simultaneously or subsequently mixed with the formulation auxiliaries.

Emulsifiable concentrates are prepared by dissolving the active ingredients in an organic solvent, for example butanol, cyclohexanone, dimethylformamide, xylene, or else higher-boiling aromatics or hydrocarbons, or mixtures of the organic solvents with the addition of one or more ionic and/or non-ionic surfactants (emulsifiers). Examples of emulsifiers which can be used are: calcium salts of alkylarylsulfonic acid such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained by grinding the active ingredients with finely divided solid substances, for example talc, natural clays such as kaolin, bentonite and pyrophyllite, or diatomaceous earth. Suspension concentrates can be water- or oil-based. They can be prepared, for example, by wet grinding using commercially available bead mills with or without addition of surfactants as have already been mentioned above, for example in the case of the other types of formulation.

Emulsions, for example oil-in-water emulsions (EW), can be prepared, for example, by means of stirrers, colloid mills and/or static mixers using aqueous organic solvents and, if appropriate, surfactants as have already been mentioned above, for example in the case of the other types of formulation.

Granules can be prepared either by spraying the active ingredients onto adsorptive granulated inert material or by applying active ingredient concentrates to the surface of carriers such as sand, kaolinites or of granulated inert material by means of binders, for example polyvinyl alcohol, sodium polyacrylate or else mineral oils. The active ingredients can also be granulated in the manner which is conventional for the production of fertilizer granules, if desired in a mixture with fertilizers.

Water-dispersible granules are generally prepared by the customary methods such as spray-drying, fluidized-bed granulation, disk granulation, mixing with high-speed mixers and extrusion without solid inert material.

In general, the mixtures according to the invention comprise 0.1 to 99% by weight, in particular 0.1 to 95% by weight, of active ingredients of the components (A) and/or (B).

The active ingredient concentration in wettable powders is, for example, approximately 10 to 90% by weight, the remainder to 100% by weight being composed of customary formulation components. In the case of emulsifiable concentrates, the active ingredient concentration may amount to approximately 1 to 90% by weight. Formulations in the form of dusts comprise, for example, 1 to 80% by weight of active ingredient, in most cases 5 to 60% by weight of active ingredient. Sprayable solutions comprise, for example, 0.05 to 80, in most cases 2 to 50, % by weight of active ingredient. The active ingredient content of water-dispersible granules depends partly on whether the active compound is in liquid or solid form and on which granulation auxiliaries, fillers and the like are being used. The active ingredient content of the water-dispersible granules amounts to, for example, between 1 and 95% by weight, in most cases between 10 and 80% by weight.

In addition, the abovementioned formulations of active ingredients comprise, if appropriate, adhesives, wetting agents, dispersants, emulsifiers, penetrants, preservatives, antifreeze agents, solvents, fillers, carriers, colorants, antifoams, evaporation inhibitors and pH and viscosity regulators, which are customary in each case.

Components which can also be used in combination with the active ingredients according to the invention in mixed formulations or in a tank mix are, for example, known active ingredients as are described, for example, in Weed Research 26, 441-445 (1986), or "The Pesticide Manual", (see above), and the literature cited therein.

For use, the formulations, which are in commercially available form, are, if appropriate, diluted in the customary manner, for example using water in the case of wettable powders, emulsifiable concentrates, dispersions and water-dispersible granules, and then applied to the plants. This includes specific application variants customary in cotton cultivation, for example the application by plane. Preparations in the form of dusts, granules for soil application or for broadcasting and also sprayable solutions are conventionally not diluted any further with other inert substances prior to use.

The invention also provides the use of the compositions or mixtures according to the invention as defoliants, i.e. for effecting leaf abscission in plants, preferably in suitable crops of useful plants, such as cotton, sunflowers or potatoes. Particular preference is given to the use as defoliant in crops of cotton.

The invention also provides a method for defoliating a plant, preferably a useful plant, particularly preferably a cotton plant, wherein the plant is treated with a mixture according to the invention or a composition according to the invention.

The invention also provides the use of the compositions or mixtures according to the invention for reducing the regrowth of plants, preferably in suitable crops of useful plants, such as cotton, sunflowers or potatoes. Particular preference is given to the use for reducing the regrowth in crops of cotton.

The invention also provides a method for reducing the regrowth of a plant, preferably a useful plant, particularly preferably a cotton plant, wherein the plant is treated with a mixture according to the invention or a composition according to the invention.

The mixtures or compositions and the methods can, of course, also be employed for treating genetically modified (transgenic) plants, preferably useful plants, particularly preferably cotton, where such plants contain, for example, one or more foreign genes in order to obtain resistance against insecticides and/or herbicides.

The invention is illustrated in more detail by the examples, without being limited thereby.

EXAMPLES

1. Preparation of the Spray Liquors

A water application rate of 300 l/ha was initially charged. The components herbicide and adjuvant were then added with stirring at the application rates and in the manner stated in the tables, such that a homogeneous spray liquor was formed. Here, the active ingredients were employed as suspension concentrates (thidiazuron as ®Escalate liquid SC500. Metribuzin as ®Sencor SC 80, thidiazuron+diuron as ®Dropp Ultra SC180) from Bayer CropScience AG. The adjuvant used was ®Actirob B (Novance).

2. Biological Tests
2.1 Test Method
Meanings of the abbreviations used below:
g of a.i./ha=gram of active ingredient/hectare
l/ha=liter/hectare Cotton seeds of the cultivar "Carmen" were sown at a depth of 1 cm and cultivated in a greenhouse cabin (20000-50000 LUX light: 14 hrs/day; temperature at night: 22° C., during the day: 30° C., rel. atmospheric humidity at night: 65%, during the day 50%) until they had reached the 6-8 leaf stage.

The plants were treated on a laboratory spray track with spray liquors of thidiazuron and thidiazuron with combination partners. The water application rate for the spray application was 300 l/ha. After the treatment, the plants were returned to the greenhouse cabin.

4 and 8 days after the application, the leaf drop effect was evaluated (leaf drop %):
0%=no noticeable effect compared to untreated plants;
100%=all leaves have dropped off.

2 weeks after the application, the regrowth of the plants was assessed by weighing the newly formed leaf material. The tabular values express the regrowth as a percentage of the untreated control.

2.2. Combinations of (A) Thidiazuron with (B) Metribuzin—Effect on Leaf Drop

The evaluations gave the results listed in table 1 which show a synergistic effect for the leaf drop effect by the combinations according to the invention.

TABLE 1

| Test 1 - Evaluation 4 and 8 days after application | | | |
|---|---|---|---|
| Components | Dose [g of a.i./ha] | Leaf drop [%] 4 days after application | Leaf drop [%] 8 days after application |
| Untreated | | 0 | 0 |
| thidiazuron* | 30 | 0 | 63 |
| metribuzin* | 15 | 0 | 0 |
| metribuzin* | 30 | 0 | 0 |
| thidiazuron + metribuzin* | 30 + 15 | 22 | 100 |
| thidiazuron + metribuzin* | 30 + 30 | 32 | 100 |

*1 l/ha of ®Actirob B was added to the spray liquors 2.3. Combinations of (A) Thidiazuron and Diuron with (B) Metribuzin—Effect on Leaf Drop The evaluations gave the results listed in table 2 which show a synergistic effect for the leaf drop effect by the combinations according to the invention.

TABLE 2

| Test 2 - Evaluation 4 and 8 days after application | | | |
|---|---|---|---|
| Components | Dose [g of a.i./ha] | Leaf drop [%] 4 days after application | Leaf drop [%] 8 days after application |
| Untreated | | 0 | 0 |
| thidiazuron + diuron* | 30 + 15 | 5 | 75 |
| metribuzin* | 15 | 0 | 0 |
| metribuzin* | 30 | 0 | 0 |
| thidiazuron + diuron + metribuzin* | 30 + 15 + 15 | 38 | 100 |
| thidiazuron + diuron + metribuzin* | 30 + 15 + 30 | 54 | 100 |

*1 l/ha of ®Actirob B was added to the spray liquors 2.4. Combinations of (A) Thidiazuron with (B) Metribuzin—Effect on the Regrowth The evaluations gave the results listed in table 3 which show a synergistic effect for the reduction of regrowth by the combinations according to the invention.

TABLE 3

| | Evaluation 2 weeks after application | |
|---|---|---|
| Components | Dose [g of a.i./ha] | Regrowth** [%] |
| metribuzin* | 15 | 0 |
| metribuzin* | 30 | 0 |
| thidiazuron* | 30 | +60 |
| thidiazuron + metribuzin* | 30 + 15 | +27 |
| thidiazuron + metribuzin* | 30 + 30 | +12 |

*1 l/ha of ®Actirob B was added to the spray liquors; repeated twice
**as a percentage of the untreated control 2.5. Combinations of (A) Thidiazuron and Diuron with B Metribuzin—Effect on Regrowth The evaluations gave the results listed in table 4 which show a synergistic effect for the reduction in regrowth by the combinations according to the invention.

TABLE 4

| | Evaluation 2 weeks after application | |
|---|---|---|
| Components | Dose [g of a.i./ha] | Regrowth** [%] |
| metribuzin* | 15 | 0 |
| metribuzin* | 30 | 0 |
| thidiazuron + diuron* | 30 + 15 | +45 |
| thidiazuron + diuron + metribuzin* | 30 + 15 + 15 | +20 |
| thidiazuron + diuron + metribuzin* | 30 + 15 + 30 | +9 |

*1 l/ha of ®Actirob B was added to the spray liquors; repeated twice
**as a percentage of the untreated control Formulation Examples (All percentages are in percent by weight based on the total weight)

1. Preparation of WP Finished Formulations:

| a) | 22% | thidiazuron |
|---|---|---|
| | 22% | metribuzin |
| | 10% | Reax 910 (dispersant: CAS No.: 068512-35-6) |
| | 2% | Nekal BX (dispersant mixture: CAS No.: 091078-64-7 and 027213-90-7) |
| | 44% | Kaolin 14030/010 (structure former: mineral filler) |
| b) | 20% | thidiazuron |
| | 10% | metribuzin |
| | 10% | Reax 910 (dispersant: CAS No.: 068512-35-6) |
| | 2% | Nekal BX (dispersant mixture: CAS No.: 091078-64-7 and 027213-90-7) |
| | 58% | Kaolin 14030/010 (structure former: mineral filler) |
| c) | 20% | thidiazuron |
| | 20% | metamitron |
| | 10% | Reax 910 (dispersant: CAS No.: 068512-35-6) |
| | 2% | Nekal BX (dispersant mixture: CAS No.: 091078-64-7 and 027213-90-7) |
| | 48% | Kaolin 14030/010 (structure former: mineral filler) |

2. Preparation of SC Finished Formulations:

| a) | 15% | thidiazuron |
|---|---|---|
| | 15% | metribuzin |
| | 6% | Soprophor FL (dispersant: CAS No.: 105362-40-1) |
| | 0.15% | Rhodopol 23 (thickener: CAS No.: 011138-66-2) |
| | 63.85% | water |
| b) | 20% | thidiazuron |
| | 10% | metribuzin |
| | 6% | Soprophor FL (dispersant: CAS No.: 105362-40-1) |
| | 0.15% | Rhodopol 23 (thickener: CAS No.: 011138-66-2) |
| | 63.85% | water |
| c) | 10% | thidiazuron |
| | 10% | metamitron |
| | 6% | Soprophor FL (dispersant: CAS No.: 105362-40-1) |
| | 0.15% | Rhodopol 23 (thickener: CAS No.: 011138-66-2) |
| | 73.85% | water |

The invention claimed is:

1. A mixture, comprising
(A) thidiazuron and optionally diuron, and
(B) metribuzin,
wherein the ratio by weight of components (A):(B) is 1:0.1 to 10.

2. The mixture as claimed in claim 1 wherein component (A) comprises thidiazuron and diuron.

3. A mixture as claimed in claim 1 that is capable of defoliating a cotton plant.

4. A mixture as claimed in claim 1 that is capable of reducing the regrowth of a cotton plant.

5. A mixture as claimed in claim 3, wherein the cotton plant comprises a transgenic cotton plant.

6. A defoliant, comprising
(A) thidiazuron and optionally diuron, and
(B) metribuzin and
(C) at least one formulation auxiliary,
wherein the ratio by weight of components (A):(B) is 1:0.1 to 10.

7. The defoliant as claimed in claim 6, wherein component (A) comprises thidiazuron and diuron.

8. A method for defoliating a cotton plant comprising treating the plant with a mixture as claimed in claim 1.

9. A method for reducing the regrowth of a cotton plant comprising treating the plant with a mixture as claimed in claim 1.

10. The method as claimed in claim 8, wherein the cotton plant is a transgenic cotton plant.

11. The method as claimed in claim 9, wherein the cotton plant is a transgenic cotton plant.

12. A method for defoliating a cotton plant and reducing regrowth of a cotton plant, comprising treating the cotton plant with
(A) thidiazuron and optionally diuron, and
(B) metribuzin,
wherein the ratio by weight of components (A):(B) is 1:0.1 to 10.

13. The method according to claim 12, wherein component (A) and component (B) are applied by successive applications.

14. A method according to claim 12, wherein component (A) is applied at a rate of 20 to 150 g of a.i/ha, and component (B) is applied at a rate of 5 to 500 g of a.i./ha.

* * * * *